US00PP20005P2

(12) United States Plant Patent
van Rysselberghe

(10) Patent No.: US PP20,005 P2
(45) Date of Patent: May 19, 2009

(54) GLOXINIA PLANT NAMED 'SONATA RED 1'

(50) Latin Name: *Sinningia speciosa*
Varietal Denomination: Sonata Red 1

(75) Inventor: Ronie van Rysselberghe, Lochristi (BE)

(73) Assignee: MicroFlor NV, Lochristi (BE)

( * ) Notice: Subject to any disclaimer, the term of this patent is extended or adjusted under 35 U.S.C. 154(b) by 0 days.

(21) Appl. No.: 12/012,935

(22) Filed: Feb. 6, 2008

Related U.S. Application Data

(60) Provisional application No. 60/872,432, filed on Jun. 26, 2007.

(51) Int. Cl.
*A01H 5/00* (2006.01)

(52) U.S. Cl. ..... Plt./482

(58) Field of Classification Search ..... Plt./482, Plt./263

See application file for complete search history.

(56) References Cited

PUBLICATIONS

UPOV–ROM GTITM, Plant Database, 2008/01, GTI Jouve Retrieval Software, citation for 'Sonata Red 1'.*

* cited by examiner

*Primary Examiner*—S. B. McCormick Ewoldt

(57) ABSTRACT

A new cultivar of Gloxinia plant named 'Sonata Red 1' that is characterized by large green leaves and red flowers.

1 Drawing Sheet

Botanical classification: *Sinningia speciosa.*
Variety denomination: 'Sonata Red 1'.

BACKGROUND OF THE INVENTION

The present invention relates to a new and distinct cultivar of Gloxinia plant botanically known as *Sinningia speciosa* and hereinafter referred to by the cultivar name 'Sonata Red 1'.

The new cultivar is the product of a breeding program conducted by the inventor in a cultivated area of Lochristi, Belgium.

'Sonata Red 1' is a hybrid that originated from the hybridization of the female or seed parent a proprietary *Sinningia speciosa* cultivar named 'A' (not patented) and the male or pollen parent a proprietary *Sinningia speciosa* cultivar named 'DSR001' (not patented). The cultivar 'Sonata Red 1' was selected by the inventor in 2003 as a single plant within the progeny of the stated cross in Lochristi, Belgium.

Asexual reproduction of the new cultivar 'Sonata Red 1' first occurred by tissue culture in 2003 in Lochristi, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Gloxinia cultivar 'Sonata Red 1'. These traits in combination distinguish 'Sonata Red 1' as a new and distinct cultivar apart from other existing known varieties of Gloxinia.

1. Gloxinia 'Sonata Red 1' exhibits large green leaves.
2. Gloxinia 'Sonata Red 1' exhibits red flowers.

The closest comparison cultivar is Gloxinia 'Amoroso Red' (not patented). 'Sonata Red 1' is distinguishable from 'Amoroso Red' by the following characteristics:

1. 'Sonata Red 1' exhibits larger flowers.
2. 'Sonata Red 1' exhibits a larger overall size.

The new cultivar 'Sonata Red 1' is distinguishable from the female parent 'A' by the following characteristics:

1. 'Sonata Red 1' exhibits double flowers.

The new cultivar 'Sonata Red 1' is distinguishable from the male parent 'DSR001' by the following characteristics:

1. 'Sonata Red 1' exhibits larger leaves.

BRIEF DESCRIPTION OF THE DRAWING

The accompanying photograph illustrates the distinguishing traits of Gloxinia 'Sonata Red 1'. The plant in the photograph shows an overall view of a 16 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new Gloxinia cultivar named 'Sonata Red 1'. Data was collected in Lochristi, Belgium from 16 week old glass greenhouse grown plants in 11 cm. diameter containers. The time of year was Fall and the temperature range was 20–22 degrees Centigrade during the day and 20–22 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Sonata Red 1' has not been tested under all possible conditions and phenotypic differences may be observed with variations in environmental, climatic, and cultural conditions, however, without any variance in genotype.

Botanical classification: *Sinningia speciosa* 'Sonata Red 1'.
Use: Ornamental Annual.
Parentage: 'Sonata Red 1' is a hybrid plant that resulted from the hybridization of the following parent plants:
*Female parent.*—*Sinningia speciosa* cultivar named 'A'.
*Male parent.*—*Sinningia speciosa* cultivar named 'DSR001'.
Vigor: Low.
Growth habit: Broad flowers in globular inflorescences.
Plant shape: Basal rosette with globular inflorescences in the center.
Suitable container size: 10 cm. pots.
Height: 15.8 cm. in height.
Width: 35.8 cm. in width.
Low temperature tolerance: USDA Zone 10.
High temperature tolerance: 40° Centigrade.
Propagation: Terminal cuttings.
Time to initiate roots: 7 days to initiate roots at 20–22° Centigrade.
Time to produce a rooted cutting or liner: 28–35 days at 20–22° Centigrade.
Crop time: 16 weeks are required to produce a finished flowering plant.
Growth rate: Approximately 5 cm. per month in spring.
Root system: Fine and fibrous.
Stem:
*Branching habit.*—No lateral branches; only basal leaves.
*Pinching.*—Not required.
Foliage:
*Texture.*—Slightly glossy and rugose.
*Leaf arrangement.*—Basal rosette.
*Compound or single.*—Single.
*Quantity of leaves.*—14.
*Leaf shape.*—Ovate to broad ovate.
*Leaf apex.*—Broad acute.
*Leaf base.*—Cordate.
*Leaf length.*—14.4 cm. in length.
*Leaf width.*—10.8 cm. in width.
*Pubescence.*—Both sides covered with short hirstute hairs, 0.2 mm, colored white to green-white.
*Leaf margin.*—Crenate.
*Young leaf color* (*lower surface*).—194A to 194B.
*Young leaf color* (*upper surface*).—139A.
*Mature leaf color* (*lower surface*).—194A to 194B.
*Mature leaf color* (*upper surface*).—139A.
*Vein color* (*under surface*).—194B, but more towards 145C to 145D.
*Vein color* (*upper surface*).—144A.
*Venation pattern.*—Pinnate.
*Leaf attachment.*—Petiolate.
*Petiole dimensions.*—3.9 cm. in length, and 7 mm. in width.
*Petiole color.*—Between 144B and 145A.
Flower:
*Inflorescence arrangement.*—Solitary flowers clustered in the center of the basal rosette.
*Flowering habit.*—Continuous.
*Quantity of flowers and buds per plant.*—48.
*Natural flowering season.*—Autumn and winter.
*Fragrance.*—None.
*Flower bud length.*—1.4 cm. in length.
*Flower bud diameter.*—1.3 cm. in diameter.
*Flower bud shape.*—Broad obovate to globular.
*Bud color.*—145A, tip 64.
*Rate of bud opening.*—10 days.
*Flower aspect.*—Upright to slightly outward.
*Flower shape.*—Funnelform.
*Flower dimensions.*—6.2 cm. in diameter and 3.2 cm. in height.
*Flower longevity.*—Approximately 7 days.
*Petal appearance.*—Glossy, velvety.
*Petal texture.*—Smooth and velvety.
*Number of petals.*—7.
*Fused or unfused.*—Only the lower 40% are fused.
*Petal shape.*—Spathulate.
*Petal margin.*—Entire, lower 40% fused.
*Petal apex.*—Rounded.
*Petal length.*—3.2 cm. in length.
*Petal width*—2.9 cm.
*Petal color when opening* (*upper side*).—In between 53A and 58A; margins and tips in between 53B and 58B, base 77B.
*Petal color when opening* (*under side*).—In between 155D and 186D; margins 63D.
*Petal color fully opened* (*upper side*).—53A, base 61A.
*Petal color fully opened* (*under side*).—59D.
*Petal color fading to.*—187A to 187B.
*Self-cleaning or persistent.*—Persistent.
Petaloids:
*Petaloid appearance.*—Smooth, velvety.
*Petaloid arrangement.*—Rotate, funnelform.
*Number of petaloids.*—Average 10.
*Petaloid shape.*—Spathulate, lower 40% fused.
*Petaloid margin.*—Entire, lower 40% fused.
*Petaloid length.*—Average 2.4 cm.
*Petaloid width.*—Average 2.5 cm.
*Young petaloid color.*—In between 53A and 58A; margins and tips in between 53B and 58A, base purple 77B.
*Mature petaloid color.*—53A, base 61A.
Sepals:
*Number of sepals.*—Average 6.
*Sepal aspect.*—Rotate.
*Sepal shape.*—Narrow ovate.
*Sepal margin.*—Entire.
*Sepal apex.*—Acute.
*Sepal base.*—Fused cuneate.
*Sepal surface.*—Glossy and pubescent, hairs 0.2 mm.
*Sepal dimensions.*—3.4 cm. in length and 1.2 cm. in width.
*Young sepal color* (*upper side*).—143A to 143B.
*Young sepal color* (*under side*).—143A.
*Mature sepal color* (*upper side*).—143A.
*Mature sepal color* (*under side*).—143B, base 143C to 143D.
Calyx:
*Calyx shape.*—Rotate.
*Calyx dimensions.*—1.2 cm. in length and 4.9 cm. in diameter.
Peduncle:
*Peduncle dimensions.*—7.3 cm. in length and 5.5 mm. in diameter.
*Peduncle angle.*—10°.
*Peduncle color.*—144A to 144B.
*Peduncle strength.*—Moderately strong.

Reproduction organs:

*Stamen number.*—Average 10.

*Anther shape.*—Strongly deformed, narrow spathulate.

*Anther size.*—Average 3 mm.

*Anther color.*—155A to 155B.

*Amount of pollen.*—None.

*Pistil number.*—Average 8.

*Pistil length.*—Average 1.8 cm. in length.

*Stigma shape.*—Club-shaped.

*Stigma color.*—N155A.

*Style length.*—1.6 cm.

*Style color.*—155D.

*Ovary color.*—155D.

Disease and pest resistance: Plants of the new cultivar have not been observed for disease and pest resistance.

It is claimed:

1. A new and distinct variety of Gloxinia plant named 'Sonata Red 1' as described and illustrated.

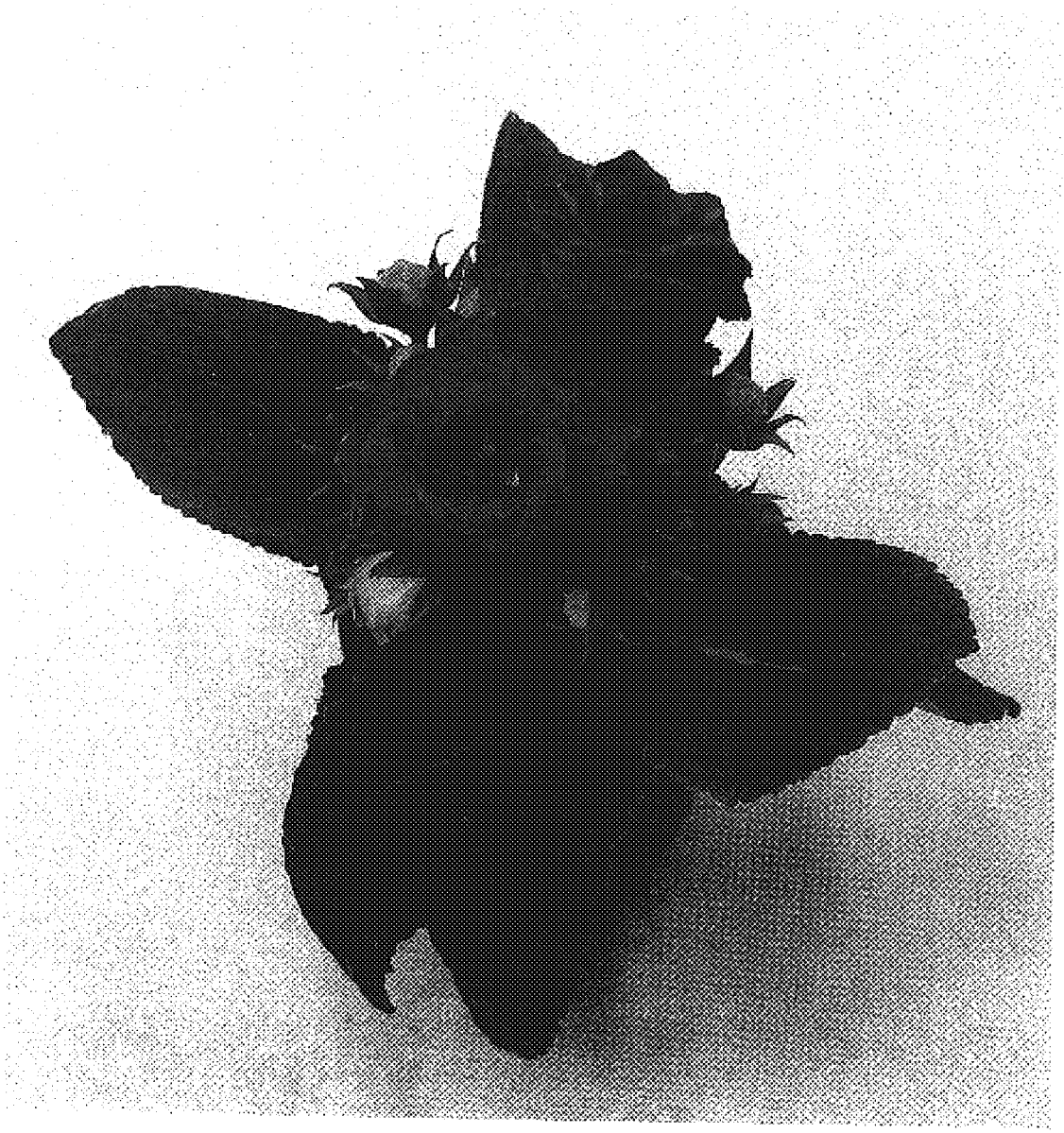

* * * * *